(12) United States Patent
Loheit

(10) Patent No.: US 10,413,104 B1
(45) Date of Patent: Sep. 17, 2019

(54) CUTLERY HOLDER WITH REMOVABLE ANTIMICROBIAL RECEPTACLE

(71) Applicant: Lawrence Jacox Loheit, Sacramento, CA (US)

(72) Inventor: Lawrence Jacox Loheit, Sacramento, CA (US)

( * ) Notice: Subject to any disclaimer, the term of this patent is extended or adjusted under 35 U.S.C. 154(b) by 223 days.

(21) Appl. No.: 15/343,830

(22) Filed: Nov. 4, 2016

Related U.S. Application Data

(63) Continuation of application No. 62/257,480, filed on Nov. 19, 2015.

(51) Int. Cl.
*A47G 21/14* (2006.01)
*A47G 29/08* (2006.01)
*A61B 50/20* (2016.01)

(52) U.S. Cl.
CPC ............ *A47G 21/14* (2013.01); *A47G 29/08* (2013.01); *A61B 50/20* (2016.02); *A47G 2400/022* (2013.01)

(58) Field of Classification Search
CPC .. A47G 21/14; A47G 29/08; A47G 2400/022; A61B 50/20
See application file for complete search history.

(56) References Cited

U.S. PATENT DOCUMENTS

| | | | | |
|---|---|---|---|---|
| 4,318,478 A | * | 3/1982 | De Winter | A47J 47/16 206/373 |
| 4,867,410 A | * | 9/1989 | Jurgich | A47G 21/14 211/70.7 |
| 6,439,403 B1 | * | 8/2002 | Levsen | A47G 21/14 211/70.7 |
| 6,854,186 B2 | * | 2/2005 | Basden | A47G 21/14 248/37.3 |
| 7,802,688 B1 | * | 9/2010 | Ruan | A47J 47/16 211/70.7 |
| 9,198,811 B2 | * | 12/2015 | Pizzato | A61F 17/00 |
| 9,693,644 B1 | * | 7/2017 | Liu | A47J 47/16 |
| 9,868,562 B2 | * | 1/2018 | McDonnell | B65D 5/4295 |

(Continued)

OTHER PUBLICATIONS http://www.williams-sonoma.com/products/shun-5-slot-modular-knife-block-set/.

*Primary Examiner* — Ko H Chan
(74) *Attorney, Agent, or Firm* — John P. Costello; Costello Law Corp.

(57) ABSTRACT

A cutlery holder adapted to providing a sanitary environment for cutlery is provided. The cutlery holder includes at least one housing and at least one receptacle/magazine. The housing is adapted to receive a removable, rotatable, reversible, interchangeable, replaceable and washable receptacle. The receptacle/magazine includes a top portion, a bottom portion, side portions and a plurality of slotted walls present in between the top and the bottom portion. The top portion and bottom portion of the receptacle/magazine includes a plurality of slots adapted to accommodate the cutleries. The side portions of the receptacle include openings that allow the flow of fluid during washing. The plurality of slotted walls provides ventilation and allows free insertion and withdrawal of the cutleries without any interference. The receptacle/magazine is anti-microbial in nature and adapted to sanitize the cutleries and other compatible articles accommodated thereto. The wide selections of receptacles allow the end user to customize the cutlery holder as per need.

15 Claims, 6 Drawing Sheets

(56) References Cited

U.S. PATENT DOCUMENTS

| | | | | |
|---|---|---|---|---|
| 2004/0148787 A1* | 8/2004 | Rosenberg | ............ | A47G 21/14 |
| | | | | 30/298.4 |
| 2005/0016886 A1* | 1/2005 | Riley | ....................... | A61C 3/04 |
| | | | | 206/438 |
| 2006/0169652 A1* | 8/2006 | Yang | ...................... | A47G 21/14 |
| | | | | 211/41.3 |
| 2012/0266468 A1* | 10/2012 | Murphy | ................. | A47G 21/14 |
| | | | | 30/298.4 |
| 2015/0257563 A1* | 9/2015 | Ludeman | ................ | A47J 47/16 |
| | | | | 211/70.7 |

\* cited by examiner

CUTLERY HOLDER WITH REMOVABLE ANTIMICROBIAL RECEPTACLE

CROSS REFERENCE TO RELATED APPLICATIONS

Provisional Patent Application Number: U.S. 62/257,480 with Filing Date: Nov. 19, 2015

FEDERALLY SPONSORED RESEARCH AND DEVELOPMENT

Not applicable.

MICROFICHE

Not applicable

BACKGROUND OF THE INVENTION

(1) Field of the Invention

The present invention relates to a cutlery holder, more particularly to a cutlery holder equipped with an anti-microbial receptacle/magazine adapted to sanitizing cutleries.

(2) Background of the Invention

Those traditional laminated wood cutlery blocks provide fixed utensil and knife slots which, through frequent use, concentrates scoring which occurs at the utensils entry-removal point. This scoring creates crevices which foster bacterial growth particularly in dark, poorly vented, warm/humid areas (cooking areas) which are part-and-parcel to hardwood blocks due to the slots position being unchangeable as well as they're being structurally and materially difficult to properly clean. Consequently, traditional wood cutlery blocks provide favorable conditions for bacterial growth and become highly unsanitary.

Various attempts have been made to solve said problems. A number of different types of cutlery holder are available in the prior art. For example, see:

WO Patent Application No. PCT/KR2007/001793 issued to Hea Ja Kim discloses a knife case equipped with a box-type body with its top open having many narrow bar-type sticks filled up in the inside of above body so that the knives can be inserted between the above stick and stick freely and supported. Further, sticks are made of Moplen RP344N polypropylene resin having the antibacterial function.

U.S. patent application Ser. No. 11/351,736 issued to Joe Glenn, Kirk Vogt, David Bridges shows an antimicrobial reusable plastic container including four polymeric sides and a polymeric base, with at least one of the sides or the bottom, is at least partially includes fabric, and where the polymeric sides, polymeric base, and/or the fabric are antimicrobial in nature.

U.S. patent application Ser. No. 08/792,155 issued to Peviani; Claudio relates to containers for cutlery and artificial jewelry generally, treated with chemical preparations whose action is antibacterial, antimycotic, and antiseptic.

U.S. patent application Ser. No. 09/264,267 issued to Hantover, Inc. relates to a utensil holder including a case and a utensil-retaining rod assembly. The case having a utensil-receiving opening and the rod assembly includes a plurality of elongated, flexible rods. The rods are confined within the utensil-receiving opening in a manner that permits limited flexing movement of the rods.

The foregoing examples of the related art disclose a general cutlery holder for accommodating different types of cutleries and articles; however cutlery holders lack an anti-microbial activity with proper ventilation and fluid flow along the cutleries. In addition, assemblies of cutlery holders present in prior arts promote bacterial growth. Therefore, there is a need of a cutlery holder that can provide an anti-microbial environment to the cutleries with proper ventilation.

In order to overcome some of these limitations, the current invention provides a cutlery holder equipped with at least one housing and at least one receptacle/magazine including a plurality of slots and slotted walls. Slots are adapted to accommodate various types of cutleries and slotted walls provide proper ventilation to the cutleries. Moreover, the receptacle is removable, rotatable, reversible, interchangeable, replaceable and washable.

The invention is directed to overcoming one or more of the problems and solving one or more of the needs as set forth above.

SUMMARY OF THE INVENTION

In the view of the foregoing disadvantages inherent in the known types of cutlery holder now present in the prior art, the present invention provides an improved cutlery holder as such, the general purpose of the present invention, which will be described subsequently in greater detail, is to provide a new and improved cutlery holder which has all the advantages of the prior art and none of the disadvantages.

This invention relates primarily to a cutlery holder adapted to house and maintain the cutlery in a highly sanitary environment. The cutlery holder includes at least one housing and at least one receptacle/magazine. The housing includes a wall with an external and an internal surface, opposite ends, and an internal hollow portion with at least one opening. The removable, rotatable, reversible, interchangeable, replaceable and washable receptacle is installed inside the internal hollow portion of the housing. The receptacle includes a top portion, a bottom portion, side portions and a plurality of slotted walls present in between the top and the bottom portion. The top portion and bottom portion of the receptacle/magazine includes a plurality of slots adapted to accommodate the cutleries. The plurality of slotted walls provides ventilation and allows free insertion and withdrawal of the cutleries without any interference. The receptacle is anti-microbial in nature and adapted to provide a highly sanitized environment to house cutlery and/or utensils.

The principal object of this invention is to provide a cutlery holder with a highly sanitary/healthy alternative to the traditional wooden cutlery block.

Another object of this invention is to provide a cutlery holder having the first line of defense against the bacterial growth.

Still another of this invention is to provide a cutlery holder having the second line of defense against the bacterial growth.

An aspect of this invention is to provide a cutlery holder including at least one housing and at least one receptacle/magazine.

Another aspect of this invention is to provide a cutlery holder including a removable, rotatable reversible, interchangeable, replaceable and washable receptacle installed in the housing.

Another aspect of this invention is to provide a cutlery holder including at least one anti-microbial receptacle providing first line defense against the bacterial growth.

Another aspect of this invention is to provide an anti-microbial receptacle including a plurality of slots and a plurality of slotted walls.

Another aspect of this invention is to provide an anti-microbial receptacle including a plurality of slots for accommodating various types of cutleries and articles.

Another aspect of this invention is to provide an anti-microbial receptacle including a plurality of slotted wall for providing the second line of defense against the bacterial growth by encouraging ventilation along the cutleries.

Another aspect of this invention is to provide an anti-microbial receptacle including a plurality of slotted walls to provide another line of defense against the bacterial growth by encouraging water flow in the cleaning process.

Another aspect of this invention is to provide an anti-microbial receptacle including a side portion having openings that allow free flow of fluids to promote cleaning.

Another aspect of this invention is to provide an anti-microbial receptacle including a plurality of slotted walls that allow free insertion and withdrawal of the cutlery without any interference.

Another aspect of this invention is to provide an anti-microbial receptacle that could be rotated, reversed and washed thereby reducing the concentration scoring and thus discouraging bacterial growth.

Another aspect of this invention is to provide a cutlery holder that could accommodate cutleries selected from but not limited to a knife and a cleaver.

Another aspect of this invention is to provide a cutlery holder including a housing that includes a plurality of slits adapted to fluid flow to promote cleaning.

Another aspect of this invention is to provide a cutlery holder that could accommodate utensils.

Another aspect of this invention is to provide a cutlery holder that could accommodate surgical instruments.

Another aspect of this invention is to provide a cutlery holder that could accommodate grooming devices.

Another aspect of this invention is to provide a cutlery holder that could accommodate ornamental articles.

Another aspect of this invention is to provide a receptacle made of anti-microbial resin.

Another aspect of this invention is to provide a cutlery holder including a housing made of a material selected from but not limited to wood, metal, and plastic.

Still another aspect of this invention is to provide an anti-microbial receptacle that is made by employing an injection mold process.

These and other objects may become more apparent to those skills in the art upon review of the summary of the invention as provided herein, and upon studying the description of its preferred embodiment, in view of the drawings.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty which characterize the invention, are pointed out with particularity in the disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural and logical changes may be made without departing from the spirit and scope of the present invention. The following detailed description is, therefore, not to be taken in a limiting sense, and the scope of the present invention is defined by the appended claims and their equivalents.

Figure 1:
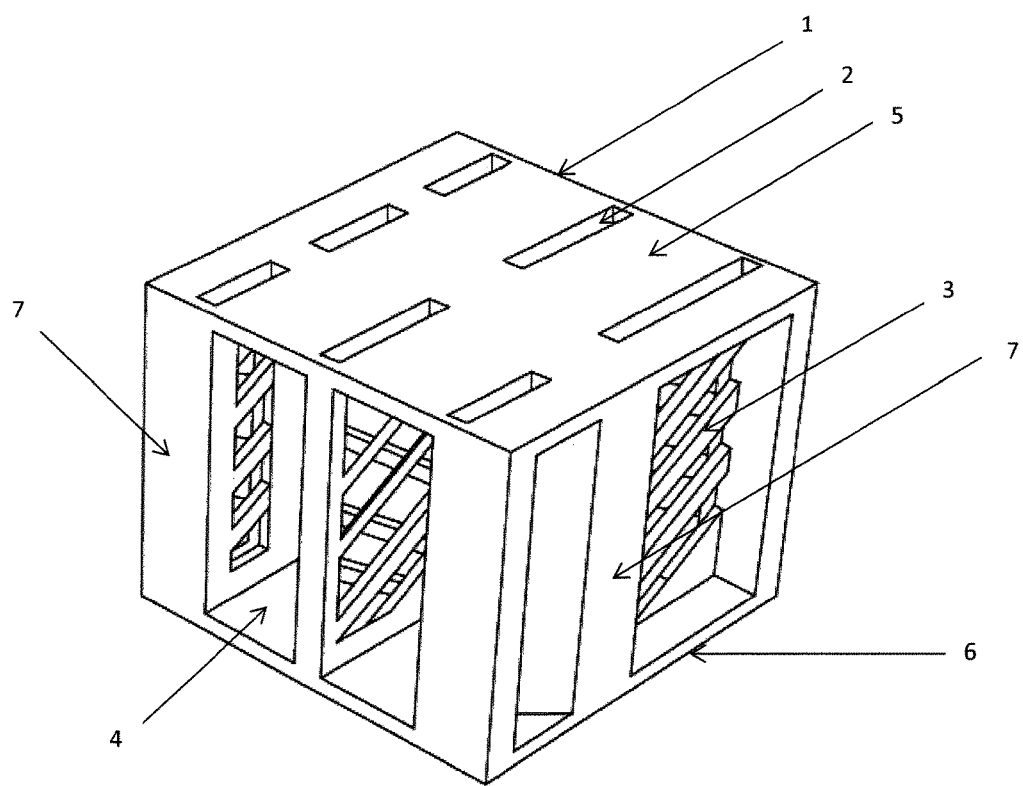
FIG. 1 shows an isometric view of an anti-microbial receptacle/magazine.
Figure 2:
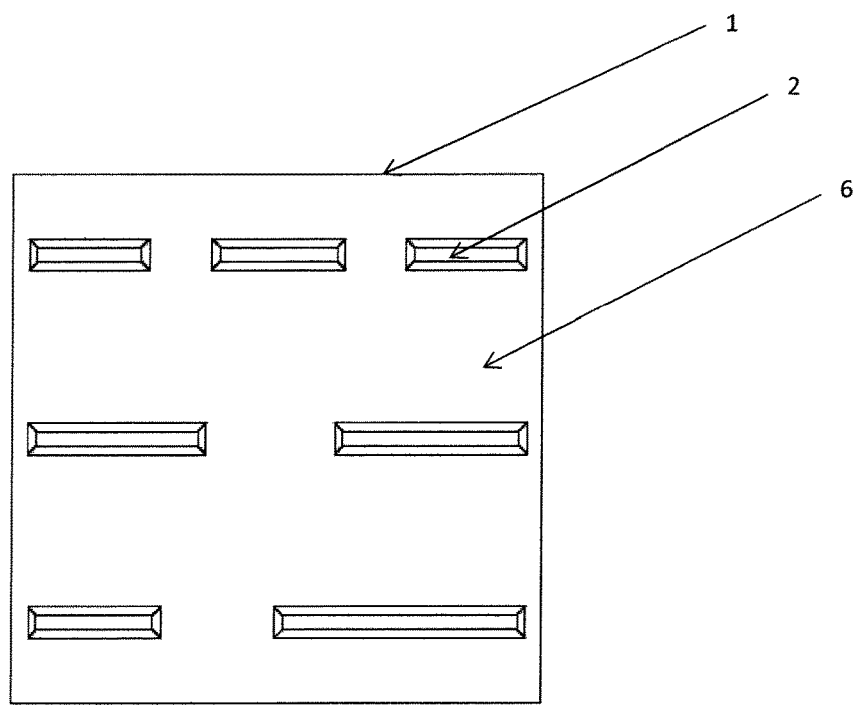
FIG. 2 shows a bottom view of an anti-microbial receptacle/magazine.

FIG. 1 and FIG. 2 illustrate a receptacle/magazine 1 made of anti-microbial resin adapted to provide a sanitary receptacle 1 to accommodate cutlery and other utensils. The receptacle 1 includes a top portion 5, a bottom portion 6, side portions 7 and a plurality of slotted walls 3 present in between the top 5 and the bottom 6 portions. The top portion 5 and bottom portion 6 of receptacle 1 includes a plurality of slots 2 adapted to accommodate the cutlery. The side portions 7 of receptacle 1 include openings 4 that allow fluid flow to promote cleaning. Further, the plurality of slotted walls 3 provide ventilation inside the receptacle 1 to discourage any bacterial growth as well as allow free insertion and withdrawal of the cutlery without any interference.

Figure 3:
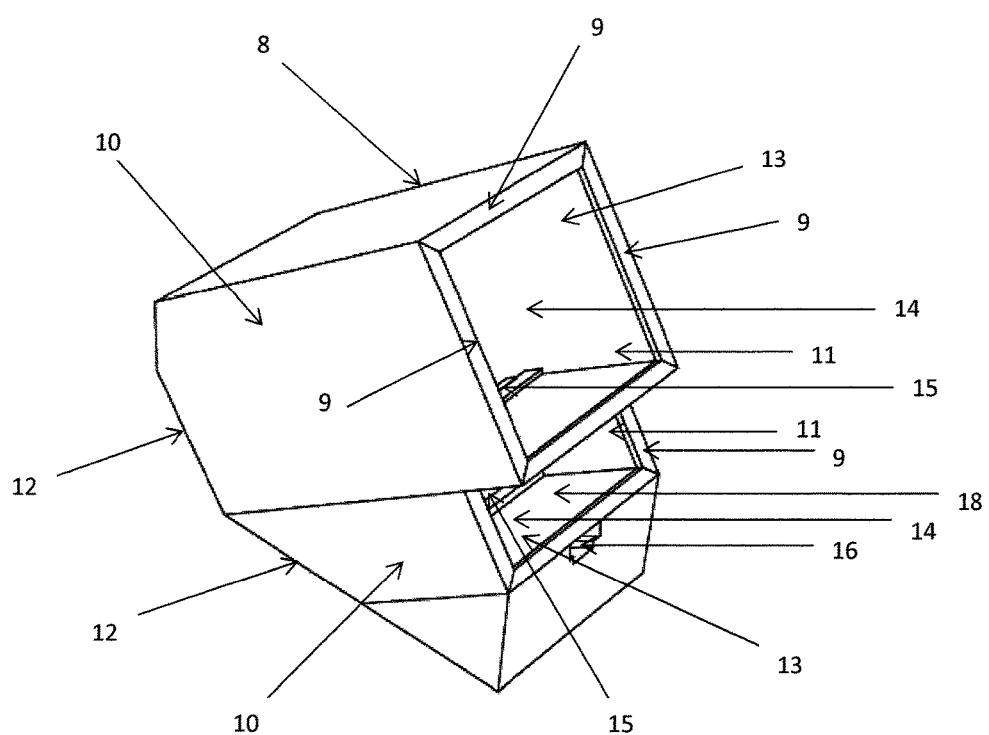
FIG. 3 shows an isometric view of a housing.
Figure 4:
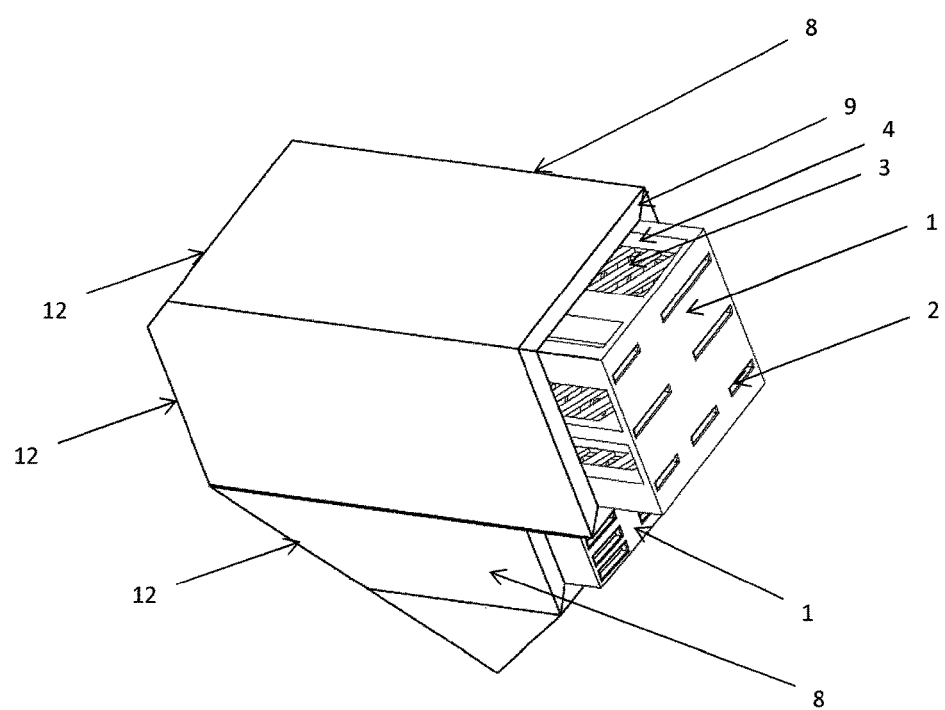
FIG. 4 shows an isometric view of a cutlery holder including partially embedded anti-microbial receptacle/magazine as shown in FIG. 1 inside the housing.

FIG. 3 and FIG. 4 depict two housings 8 where each one is adapted to receive a receptacle/magazine 1. Each housing 8 includes a wall 9 with an external 10 and an internal 11 surface, two opposite ends that are an open end 13 and a closed end 12, and an internal hollow portion 14. Further, each housing unit 8 includes a raise ridge 15 to prevent receptacle 1 from slipping beyond the desired distance. In addition, housing 8 has an extra compartment 16 for receiving a pair of kitchen scissors.

Referring to FIG. 4 illustrates a cutlery holder including partially embedded receptacles/magazines 1 inside the housings 8. The housings 8 includes a wall 9 with an external 10 and an internal 11 surface as shown in FIG. 3, two opposite ends that are an open end 13 and a closed end 12, and an internal hollow portion 14 as shown in FIG. 3. Further, receptacles/magazine 1 includes a top portion 5, a bottom portion 6, side portions 7 as shown in FIG. 1 and a plurality of slotted walls 3 present in between the top 5 and the bottom 6 portions. The top portion 5 and bottom portion 6 of receptacle 1 as shown in FIG. 1 includes a plurality of slots 2 adapted to accommodate the cutlery. The side portions 7 of receptacle 1 include openings 4 that allow fluid flow to promote cleaning.

Figure 5:
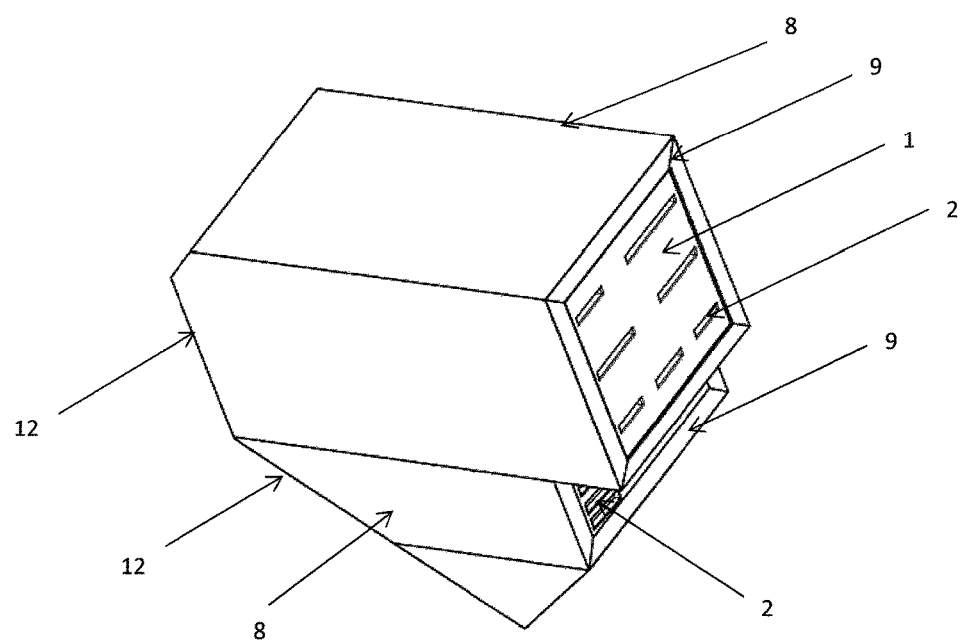
FIG. 5 shows an isometric view of a cutlery holder including fully embedded anti-microbial receptacle/magazine as shown in FIG. 1 inside the housing.
Figure 6:
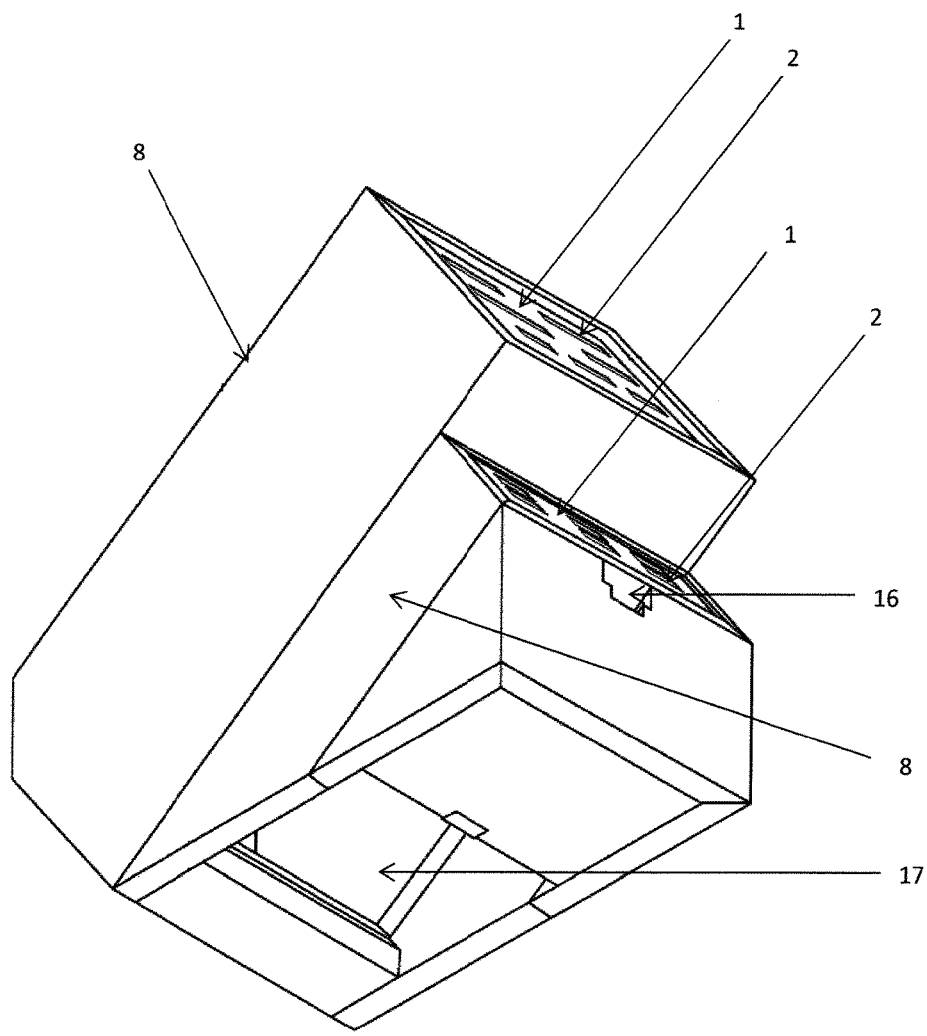
FIG. 6 shows a bottom view of a cutlery holder including fully embedded anti-microbial receptacle/magazine as shown in FIG. 1 inside the housing.

Referring to FIG. 5 and FIG. 6 depict a cutlery holder including fully embedded receptacles/magazines inside the housings. The housings 8 includes a wall 9 with an external 10 and an internal 11 surface as shown in FIG. 3, two opposite ends that are an open end 13 and a closed end 12, and an internal hollow portion 14 as shown in FIG. 3. Further, receptacles/magazine 1 includes a top portion 5, a bottom portion 6, side portions 7 as shown in FIG. 1 and a plurality of slotted walls 3 present in between the top 5 and the bottom 6 portions. The top portion 5 and bottom portion 6 of receptacle 1 as shown in FIG. 1 includes a plurality of slots 2 adapted to accommodate the cutlery. The side portions 7 of receptacle 1 include openings 4 that allow fluid flow to promote cleaning. Further, an extra compartment 16 is present for receiving a pair of kitchen scissors as shown in FIG. 6. In addition, a gap at bottom 17 for encouraging ventilation and cleaning inside the cutlery holder.

In one of the most preferred embodiment cutlery holder includes two housings 8 and two receptacles/magazines 1 made of anti-microbial resin for sanitizing the accommodated cutleries. Exterior 10 and interior 11 walls 9 (panels) of double housings 8 are most commonly constructed using a plurality of wood materials measuring approximately ½ inch in thickness. The outside dimensions of the housing are 5½ inches wide, 11 inches high and 11¼ inches deep. Double housings include a larger square shaped housing 14 and a smaller rectangular 18 shaped housing 8. Both larger 14 and smaller 18 housings are at a 35-degree angle from the base of the double housing section. The front openings 13 of each housing are 1/16 of an inch larger laterally and 1/16 of an inch larger vertically than the receptacle it will receive, allowing entry of the corresponding receptacle. The depth of both the double housing sections larger square and smaller rectangular shaped opened ends are reduced in size at a distance of ⅛ of an inch greater than the depth of the receptacle 1 it is receiving thusly preventing the receptacle 1 from being inserted more than ⅛ of an inch beyond the front outermost portion of the open-end 13 receptacles entry point at the exterior face of the double housing sections openings. The receptacles 1 are free to slide into their respective front opened-ends 13 of the double housing section. The most extreme bottom panel of double housing section are flat and raised from the flat surface each may rest upon by four ⅛ inch thick (high) by ⅜ inch diameter (wide) legs; one placed near the extreme four corners of the bottom panel of the housing section. The gap created by the ⅛ inch high legs raises the entire housing section ⅛ inch above the flat surface on which the housing 8 section is placed. The bottom of the double housing 8 section has a large gap 17 of 4 inches or break in the bottom panel equal to the full interior width between the exterior left and right ½ inch panels of the bottom panel to allow air flow and of sufficient breadth to allow easy access to the back faceplate of the receptacles 1 thusly allowing a means to push the receptacles 1 out through the housing sections entry opening should the receptacle not slide-out when the housing section is tilted to allow the receptacles 1 to freely slip-out. Further, receptacles/magazines 1 made of anti-microbial resin that stops 96% to 98% of the bacteria from attaching itself to the resin. Receptacles are of two shapes and sizes one is larger for square shaped housing 14 and another one is for smaller for rectangular shape housing 18. The larger square-shaped receptacle 1 has $4^{7/16}$ inch sides and 3½ inch deep. Both receptacles 1 have a plurality of spaced slots 2 formed therein of various widths and breadths to accommodate 5 to 11 cutlery knives up to 10 inches in length and other kitchen utensils, and sharpening tools.

In some of the embodiment, the cutlery holder includes a single housing 8 section with a single anti-microbial resin receptacle 1. The single housing 8 section is limited to housing one larger square-shaped receptacle 1. The single housing 8 sections exterior 10 and interior 11 walls 9 (panels) are most commonly constructed using a plurality of wood materials measuring approximately ½ inch in thickness. The front open end 13 of the single housing 8 section is at a 35-degree angle from the base of the single housing 8 section. The single housing 8 section has a front opening which is 1/16 of an inch laterally and 1/16 of an inch vertically larger than the larger square shaped receptacles thusly allowing entry of the larger square-shaped receptacle. Receptacle 1 has a plurality of spaced slots 2 formed therein of various widths and breadths to accommodate a plurality of cutlery knives and other kitchen utensils, and sharpening tools. The receptacle 1 is free to slide into the front open end 13 of the single housing 8 section. The depth of the single housing 8 sections opened-end 13 is reduced in size by ⅛ of an inch at a distance of ⅛ of an inch greater than the depth of the receptacle 1 it is receiving, thusly preventing the receptacle 1 from being inserted more than ⅛ of an inch beyond the front outermost portion of the open-end 13 receptacles 1 entry point at the exterior 10 face of the single housing section 8.

In some of the embodiment, the larger square-shaped receptacle 1 has $4^{7/16}$ inch sides and 3½ inch deep and has a plurality of spaced slots 2 formed therein of various widths and breadths to accommodate a plurality of cutlery knives and other kitchen utensils. The larger square-shaped receptacle 1 exhibits a perfectly square front 5 and back 6 portions. Being of equal width and breadth allows the receptacle 1 to be rotated in four different positions in the housing 8 section. The larger square-shaped receptacle 1 front 5 and back 6 portions are identical in shape, design, and construction that allows the receptacle 1 to be reversed (turned from front to back) and rotated again for an additional four different positions, representing a totality of eight possible receptacles 1 resting positions. The rotation of the larger square-shaped receptacle 1 reduces the concentration of scoring which causes crevices to form at the entry and removal contact points of the slots during entry and removal of the utensils. The eight possible receptacle 1 positions in the housing sections larger square-shaped receptacle opening reduce the concentration of scoring caused by the entry and removal of utensils by up to 87.5% thusly leaving a cleaner, newer appearance much longer than traditional cutlery holders.

In some of the embodiment, the smaller rectangular shaped receptacle 1 has a plurality of spaced slots 2 formed therein of various widths and breadths to accommodate a plurality of steak knives and other kitchen utensils. The smaller rectangle shaped receptacle 1 front 5 and back 6 portions are identical in shape, design, and construction which allows the receptacle 1 to be turned upside-down and then reversed (turned from front to back) and turned up-side-down again representing a total of four possible receptacle resting positions. The rotation of the smaller rectangular shaped receptacle 1 reduces the concentration of scoring which causes crevices to form at the entry and removal contact points of the slots during entry and removal of the utensils. The four possible receptacle positions in the housing sections smaller rectangular shaped receptacle 1 opening reduce the concentration of scoring caused by the entry and removal of utensils by up to 75% thusly leaving a cleaner, new appearance much longer than traditional cutlery holder.

In some of the embodiment, the receptacles 1 are designed to provide durability and strength. Receptacles have front and back faceplates are no less than 3/16 inch thick and made of solid anti-microbial resin. The physical dimension of receptacles ranges from 4½-5½ inches length, 1½-5½ inches width and 3-6 inches deep. The four corner post and a plurality of joint post on each side of a receptacles slot 2 provide additional support to securely join the front faceplate to the back faceplate in various thicknesses none being neither less than 1/8 inch thick nor more than ½ inch thick made of a solid anti-microbial resin providing additional strength and durability.

In some of the embodiment, the receptacles 1 are designed to provide maximum airflow without compromising strength and durability. The receptacles 1 interior slotted walls 3 are 1/8 inch thick solid anti-microbial resin specifically designed to provide maximum airflow/ventilation while allowing the utensils to be freely inserted and removed without interference from the slotted interior walls of the receptacles 1. The receptacles 1 airflow design also provides the maximum flow of water to allow an efficient and effective cleaning to provide maximum cleaning results.

In some of the embodiment the method to prepare anti-microbial resin receptacle 1 involves employing of anti-microbial resin into a mold using an injection process. Mold could be of different shape and size depending upon the shape and size of the housing 8 sections.

According to the present invention, the receptacle/magazine 1 should be removed from the housing prior to any cleaning. The receptacles/magazines 1 are designed to be totally submersible and provide thorough drainage and ventilation which compliments the anti-bacterial objectives. The housing 8 should not be subjected to liquid washing. Both water and high heat will cause serious damage to wooden housing and to any natural product. Wood products should be carefully cleaned with a dry dust cloth and periodically cleaned using wood/furniture cleaning products.

According to the present invention, to remove the receptacle/magazine 1 from the housing, first carefully remove the entire cutlery set from the receptacle/magazine 1 and all contents, lids, covers, and any drawer from the housing 8. Tip the empty housing 8 to allow the receptacle/magazine 1 to safely slide out of the housing. If it is difficult to remove the receptacle/magazine 1 from the housing 8, simply reach up and through the gap 17 under the lower portion/compartment of the receptacle/magazine 1 and push-up and out on the backside of the receptacle/magazine 1.

According to the present invention, to wash the receptacle/magazine 1 the best way is hand washing, after submerging into soapy water. Make sure the receptacle/magazine is totally dry before placing it back into the housing.

According to the present invention, the housing section of the manufacturing material of cutlery holder is selected from but not limited to wood, metal, and plastic. The manufacturing material of the receptacle is selected from the most current and effective anti-microbial resin.

Alternatively, the shape and size of the housing sections and receptacles could be cylindrical or trapezius. The number of opening and closing end of the housings would vary according to the shape of cutlery holders.

Advantageously the cutlery holder of the present invention provides a sanitizing mechanism for all types of cutleries, utensils, surgical instruments, grooming tools, ornamental articles and sharpening tools. Anti-microbial receptacles/magazines fit into the various housings that come in a variety of configurations and can pretty much accommodate any number of cutleries and other compatible articles. Further, rotatable, transversible, interchangeable, replaceable and washable feature of the receptacle discourages any bacterial growth inside cutlery holder. Moreover, ventilation and proper flow of fluid assists in discouraging the bacterial growth and keep cutleries and other articles clean and fresh.

It is to be understood that the above description is intended to be illustrative, and not restrictive. For example, the above-discussed embodiments may be used in combination with each other. Many other embodiments will be apparent to those of skill in the art upon reviewing the above description.

The benefits and advantages which may be provided by the present invention have been described above with regard to specific embodiments. These benefits and advantages and any elements or limitations that may cause them to occur or to become more pronounced are not to be construed as critical, required, or essential features of any or all of the embodiments.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention.

What is claimed is:

1. A cutlery holder adapted to providing a sanitary environment for at least one cutlery, comprising:
    at least one housing, wherein said housing includes a wall with an external and an internal surface, opposite ends, an internal hollow portion with at least one opening thereto, and a base, said base having a bottom surface for engaging with a substantially planar external surface, said internal hollow portion being supported by said base, said internal hollow portion being disposed at an angle relative to said base; and
    at least one receptacle, wherein said receptacle is removably installed inside said internal hollow portion of said housing, said receptacle includes a top portion, a bottom portion, side portions and a plurality of slotted walls present in between said top and said bottom portion,
    said top portion includes a plurality of slots adapted to accommodate said cutlery,
    said bottom portion includes a plurality of slots adapted to accommodate said cutlery,
    said side portions of said receptacle include openings adapted to provide fluid flow to promote cleaning,
    said plurality of slotted walls providing ventilation to discourage a bacterial growth, said plurality of slotted walls allowing free insertion and withdrawal of said cutlery without any interference, said receptacle being anti-microbial in nature adapted to sanitize said cutlery accommodated thereto.

2. The cutlery holder adapted to providing a sanitary environment for at least one cutlery of claim 1, wherein said cutlery is selected from the group consisting of a knife, and a chopper.

3. The cutlery holder adapted to providing a sanitary environment for at least one cutlery of claim 1, wherein said cutlery holder is adapted to accommodate a utensil.

4. The cutlery holder adapted to providing a sanitary environment for at least one cutlery of claim 1, wherein said cutlery holder is adapted to accommodate a surgical instrument.

5. The cutlery holder adapted to providing a sanitary environment for at least one cutlery of claim 1, wherein said cutlery holder is adapted to accommodate a grooming tool.

6. The cutlery holder adapted to providing a sanitary environment for at least one cutlery of claim 1, wherein said cutlery holder is adapted to accommodate an ornamental article.

7. The cutlery holder adapted to providing a sanitary environment for at least one cutlery of claim 1, wherein said wall of said housing includes a plurality of gaps adapted for fluid flow to promote cleaning.

8. The cutlery holder adapted to providing a sanitary environment for at least one cutlery of claim 1, wherein said receptacle is removable from said internal hollow portion of said housing, said receptacle being rotatable into four alternate positions and re-insertable into said internal hollow portion of said housing in one of said four alternate positions.

9. The cutlery holder adapted to providing a sanitary environment for at least one cutlery of claim 1, wherein said receptacle is removable from said internal hollow portion of said housing, said receptacle being transversable and re-insertable into said internal hollow portion of said housing in a transverse position.

10. The cutlery holder adapted to providing a sanitary environment for at least one cutlery of claim 1, wherein said receptacle is washable to discourage said bacterial growth.

11. The cutlery holder adapted to providing a sanitary environment for at least one cutlery of claim 1, wherein said receptacle is made of an anti-microbial resin.

12. The cutlery holder adapted to providing a sanitary environment for at least one cutlery of claim 1, wherein manufacturing material for said housing is selected from the group consisting of wood, metal, and plastic.

13. The cutlery holder adapted to providing a sanitary environment for at least one cutlery of claim 1, wherein said internal hollow portion is disposed at approximately a 35-degree angle relative to said base.

14. The cutlery holder adapted to providing a sanitary environment for at least one cutlery of claim 1, wherein said base is adapted to accommodate an extra compartment for receiving a pair of kitchen scissors.

15. A cutlery holder adapted to providing a sanitary environment for at least one cutlery, comprising:
    a first housing, wherein said first housing includes a wall with an external and an internal surface, opposite ends, and an internal hollow portion with at least one opening thereto;
    a second housing, wherein said second housing includes a wall with an external and an internal surface, opposite ends, and an internal hollow portion with at least one opening thereto;
    a base, said base having a bottom surface for engaging with a substantially planar external surface, said first and second housings being supported by said base, said internal hollow portions of said first and second housings being disposed at an angle relative to said base;
    a first receptacle, said first receptacle being removably installed inside said internal hollow portion of said first housing, said first receptacle including a top portion, a bottom portion, side portions and a plurality of slotted walls present in between said top and said bottom portion,
    a second receptacle, said second receptacle being removably installed inside said internal hollow portion of said second housing, said second receptacle including a top portion, a bottom portion, side portions and a plurality of slotted walls present in between said top and said bottom portion,
    said top portion of said first and second receptacles including a plurality of slots adapted to accommodate said cutlery,
    said bottom portion of said first and second receptacles including a plurality of slots adapted to accommodate said cutlery,
    said side portions of said first and second receptacles including openings adapted to provide fluid flow to promote cleaning,
    said plurality of slotted walls providing ventilation to discourage a bacterial growth, said plurality of slotted walls allowing free insertion and withdrawal of said cutlery without any interference,
    said first and second receptacles being anti-microbial in nature adapted to sanitize said cutlery accommodated thereto.

* * * * *